(12) United States Patent
Carver, Jr. et al.

(10) Patent No.: US 6,812,032 B1
(45) Date of Patent: *Nov. 2, 2004

(54) APPARATUS AND METHOD FOR MAKING A PLURALITY OF REAGENT MIXTURES AND ANALYZING PARTICLE DISTRIBUTIONS OF THE REAGENT MIXTURES

(75) Inventors: Edward Lawrence Carver, Jr., Oxford, CT (US); David Charles DeCava, Oxford, CT (US)

(73) Assignee: CDC Technologies, Inc., Oxford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/039,789

(22) Filed: Mar. 16, 1998

Related U.S. Application Data

(60) Continuation of application No. 08/370,023, filed on Jan. 9, 1995, now Pat. No. 5,728,351, which is a division of application No. 08/007,111, filed on Jan. 21, 1993, now Pat. No. 5,380,491.

(51) Int. Cl.[7] ............................................. G01N 33/48
(52) U.S. Cl. ........................... 436/63; 422/67; 422/73; 422/81; 422/100; 436/8; 436/17; 436/18; 436/52; 436/66; 436/174; 436/175
(58) Field of Search .................. 436/8, 17–18, 436/52, 63, 66, 174–175; 417/568; 422/67, 73, 81, 100

(56) References Cited

U.S. PATENT DOCUMENTS

| | | |
|---|---|---|
| 3,793,587 A | 2/1974 | Thom et al. |
| 3,810,010 A | 5/1974 | Thom |
| 3,822,095 A | 7/1974 | Hirschfeld |
| 3,836,849 A | 9/1974 | Coulter et al. |
| 3,871,770 A | 3/1975 | von Behrens et al. |
| 3,900,290 A | 8/1975 | Hornstra |
| 4,001,678 A | 1/1977 | Berg |

(List continued on next page.)

FOREIGN PATENT DOCUMENTS

| | | |
|---|---|---|
| EP | 0 101 161 | 2/1984 |
| EP | 0 107 333 | 5/1984 |
| EP | 89/04961 | 6/1989 |
| EP | 398652 | * 11/1990 |

OTHER PUBLICATIONS

M. P. Natt et al, Poultry Science 1952, 31, 735–738.*
J. A. O'Daly et al, Exp. Parasitol. 1979, 47, 222–231.*

(List continued on next page.)

*Primary Examiner*—Arlen Soderquist
(74) *Attorney, Agent, or Firm*—McCarter & English, LLP

(57) ABSTRACT

An apparatus is provided for hematology testing, which has a sensing unit defining a counting orifice for the flow of a blood sample through the counting orifice to analyze the blood sample, and a pump unit having three syringes. A first syringe is coupled in fluid communication with the sensing unit on the inlet side of the counting orifice for injecting a stream of blood sample through the counting orifice. A second syringe is coupled in fluid communication with the sensing chamber on the inlet side of the counting orifice for simultaneously injecting a sheath of fluid surrounding the sample stream on the inlet side of the counting orifice. And a third syringe is coupled to the sensing chamber on the outlet side of the counting orifice for aspirating a sheath of fluid from the sensing chamber surrounding the sample stream on the outlet side of the counting orifice. A control unit is connected to the pump unit for adjusting the reagent mixture to correspond to each of a plurality of different operator inputs, wherein each operator input may correspond to a respective animal species, to automatically create and analyze the reagent mixture for each animal species.

14 Claims, 4 Drawing Sheets

U.S. PATENT DOCUMENTS

| | | |
|---|---|---|
| 4,014,611 A | 3/1977 | Simpson |
| 4,030,888 A | 6/1977 | Yamamoto et al. |
| 4,050,904 A | 9/1977 | Cramer |
| 4,146,604 A | 3/1979 | Kleinerman |
| 4,165,484 A | 8/1979 | Haynes |
| 4,198,160 A | 4/1980 | Kachel et al. |
| 4,253,058 A | 2/1981 | Kachel et al. |
| 4,323,537 A | 4/1982 | Mody |
| 4,395,676 A | 7/1983 | Hollinger et al. |
| 4,420,564 A | 12/1983 | Tsuji et al. |
| 4,424,276 A | 1/1984 | Clark et al. |
| 4,428,669 A | 1/1984 | Bessis .......................... 356/39 |
| 4,503,385 A | 3/1985 | Haynes |
| 4,509,904 A | 4/1985 | MacAskill et al. |
| 4,606,631 A | 8/1986 | Anno et al. .................... 356/36 |
| 4,634,431 A | 1/1987 | Whitney et al. |
| 4,683,212 A | 7/1987 | Uffenheimer |
| 4,695,431 A | 9/1987 | Farrell |
| 4,713,974 A | 12/1987 | Stone |
| 4,727,042 A * | 2/1988 | Mitzner et al. ................ 436/10 |
| 4,779,976 A * | 10/1988 | Levine et al. .................. 356/39 |
| 4,908,187 A | 3/1990 | Holmquist et al. |
| 4,948,565 A | 8/1990 | Bemis et al. |
| 5,003,895 A | 4/1991 | Talanker |
| 5,030,002 A | 7/1991 | North, Jr. |
| 5,092,989 A | 3/1992 | Steen |
| 5,134,079 A | 7/1992 | Cusack |
| 5,180,677 A | 1/1993 | Di Ianni et al. |
| 5,187,673 A | 2/1993 | Carver, Jr. et al. |
| 5,223,398 A | 6/1993 | Kortright et al. |
| 5,256,374 A | 10/1993 | De Silva et al. |
| 5,260,027 A | 11/1993 | Kuroda |
| 5,262,329 A * | 11/1993 | Carver, Jr. .................... 436/63 |
| 5,316,725 A | 5/1994 | Carver, Jr. et al. |
| 5,728,351 A * | 3/1998 | Carver, Jr. .................... 422/73 |

OTHER PUBLICATIONS

M. L. Tyan Mech. Ageing Dev. 1982, 20, 25–32.*
R. P. Dales Comp. Biochem. Physiol. 1982, 73A, 663–667.*
M. R. Kasschau et al, Exp. Parasitol. 1986, 61, 201–209.*
M. R. Kasschau et al, Comp. Biochem. Physiol. 1988, 90A, 453–458.*
M. R. Kasschau et al, Comp. Biochem. Physiol. 1991, 96B, 195–200.*
M. I. Tiirikainen et al, Ann. Hematol. 1992, 65, 124–130.*
G. F. Orthey et al, UR Reports Mar. 1965, 51, 1–9.*
J. Brotherton Andrologia Mar. 1975, 7, 169–185.*
R. B. Scott et al, Blood Jun. 1978, 51, 1137–1148.*
W. G. Halliday et al, Med. Lab. Sci. 1979, 36, 353–358.*
G. W. Robertson et al, British Poultry Science Dec. 1990, 31, 881–886.*
L. W. M. M. Terstappen et al, Blood Cells 1991, 17, 585–605.*
K. S. Latimer et al, Avian Diseases Oct. 1988, 32, 760–772.*
L. W. M. M. Terstappen et al, J. Immunolog. Methods Sep. 1989, 123, 103–112.*
M. E. Fowler et al, Am. J. Vet. Sci. Dec. 1989, 50, 2049–2053.*
B. A. Naughton et al, J. Lab. Clin. Med. Oct. 1990, 115, 498–507.*
M. G. Veiser Am. J. Vet. Res. Jan. 1982, 43, 163–166.*
W. Groner et al, Blood Cells Dec. 1986, 12, 65–80.*
M. G. Weiser Vet. Pathol. Nov. 1987, 24, 560–563.*
L. W. M. M. Terstappen et al, Cytometry 1988, 9, 548–556.*
T. Nishikawa et al. J. Osaka. Odontol. Soc. Feb. 1985, 48, 78–87.*
T. Nishikawa et al. J. Osaka Odontol. Soc. Feb. 1985, 48, 88–98.*
M. G. Weiser *JAVMA* 1987, 190, 411–415.*
M. B. Callan et al. *Am. J. Vet. Res,* 1992, 53, 1760–1764.*
J.B. Dixon et al. *Res. Vet. Sci.* 1981, 31, 249–252.*
J.M. England et al. *Clin. Lab. Haematol.* 1982, 4, 187–199.*
G. Valet *Blut* 1984, 49, 83–90.*
R.L. Talley et al, *Res. Commun. Chem. Path. Pharm.* 1987, 55, 117–131.*
B.A. Payne et al. *Am. J. Clin. Path.* 1987, 88, 51–57.
Fisher Scientific Catalog 1988, pp. 1403–1402.
R. Hallawell et al. *Am. J. Clin. Path.* 1991, 96, 594–601.
The Henley Group Inc., "The CELLECT™ Hematology Systems From Instrumentation Labratory", 1986.
I.W. Taylor et al. *J. Histochem. Cytochem.* 1980, 28, 1224–1232.
K. Hagino et al. *Jikken Dobutsu Experimental Animals* 1982, 31, 259–264.
K. Matsumoto et al. *Jikken Dobutsu Experimental Animals* 1983, 32, 115–122.
D.M. Popp et al. *J. Foxicol. Environ. Health* 1986, 18, 543–565.
M. Hageltorn et al. *Am. J. Vet. Res.* 1986, 47, 2012–2016.
F.I. Wang et al. *Can. J. Vet. Res.* 1987, 51, 421–427.
A.M. Saad et al. *J. Vet. Med. B.* 1989, 36, 337–345.
G.A. Dean et al. *Vet. Immunol. Immunopathol.* 1991, 28, 327–336.

* cited by examiner

APPARATUS AND METHOD FOR MAKING A PLURALITY OF REAGENT MIXTURES AND ANALYZING PARTICLE DISTRIBUTIONS OF THE REAGENT MIXTURES

This patent application is a continuation of U.S. patent application Ser. No. 08/370,023, filed Jan. 9, 1995, herewith now U.S. Pat. No. 5,728,351 which is a divisional of U.S. patent application Ser. No. 08/007,111, filed Jan. 21, 1993, now U.S. Pat. No. 5,380,491, both of which are hereby expressly incorporated by reference as part of the present disclosure.

FIELD OF THE INVENTION

The present invention is directed to apparatus and methods for making reagent mixtures, and more particularly, to apparatus and methods for making a plurality of reagent mixtures and analyzing particle distributions of the reagent mixtures, such as for blood cell analysis.

BACKGROUND INFORMATION

Prior to the mid-1970s, red blood cell, platelet and white blood cell differential analyses were typically conducted by manual examination, with a technician viewing blood film slides with the aid of a microscope. Since that time, hematological analysis has been automated, making its use both widespread and commonplace.

While the methodologies for automated analysis vary, most often the enumeration and analysis involves subjecting a diluted sample of whole blood to a lysing reagent which stromatolyzes and eliminates the red blood cell population, and simultaneously modifies the cell membranes of the more prevalent white cell subpopulations. This causes differential shrinkage of the different cell types and enables discrimination and sorting thereof. The size and number of white blood cells in the sample are then detected with the aid of an automated analyzer, by pulling the sample fluid through a sensing zone, which is typically adapted to detect the size (volume) and/or opacity of the blood cells in the sample by electrical or optical differences. The blood cells are counted for a period of time sufficient to gather data for analysis, data points are stored in a memory device, and then analyzed in a processor. The data can then be displayed in the form of a two-dimensional or three-dimensional histogram.

There are various prior art devices for supplying sheath stream and sample fluids to the sensing aperture of a detector. U.S. Pat. No. 3,740,143 shows a system employing peristaltic pumping to supply a series of diluted blood samples to a flow cell for white blood cell differentiation and counting. Peristaltic pumping, which operates by the occlusion or squeezing of the pump tubes, does not provide a sufficiently steady-state flow, and can result in damage to the integrity of the cells, further degrading the accuracy of the device.

U.S. Pat. No. 4,695,431 also shows an apparatus for supplying fluids to a sheath stream flow cell, which employs a single piston pump to inject the sheath fluid into the flow cell with one side of the pump, and simultaneously aspirate the blood sample through the flow cell with the other side of the pump. The piston pump is driven by a drive cylinder operated by controlling the flow of pressurized fluid. By aspirating the blood sample through the flow cell, the suction forces can distort the cells, thus reducing the accuracy of the device. Also, because the single pump is driven by a pressurized cylinder, the fluid quantity cannot be controlled as accurately as may be desired.

For cell or particle analyses of this type, the present inventors have realized that it is advantageous to detect one cell at a time, and accumulate data on thousands of cells. Coincidence, or the simultaneous passage of multiple cells through the sensing zone, can create anomalies or aberrant information. Although this type of information can be partially corrected by using mathematical equations or pulse editing circuits when analyzing the data, important information about the cells may be rejected and thrown away with the sample. This may include information about abnormalities in the sample, since the abnormal cells may give rise to unusual pulses that are rejected in compensating for the passage of multiple cells through the sensing zone. The present inventors have realized that it would be desirable to provide a precisely controlled, steady-state flow of both blood sample and sheath fluids, wherein the sample cells are injected through the sensing zone in a substantially single-file relationship relative to each other in order to avoid coincidence and permit accurate detection of cell properties.

The present inventors have also realized that it would be desirable to provide an apparatus and method for hematology testing that may automatically adjust or create reagent mixtures corresponding to each of a plurality of different species.

SUMMARY OF THE INVENTION

The present invention is directed to an apparatus and method for making a plurality of reagent mixtures and analyzing particle distributions of the reagent mixtures, such as for blood cell analysis. The apparatus comprises at least one pump, such as a positive-displacement pump, a sensing unit defining a counting orifice for receiving a reagent mixture and analyzing a particle distribution of the reagent mixture, and a control unit, or like means, for adjusting the reagent mixture to correspond to each of a plurality of different operator inputs. The control unit controls one or more pumps to aspirate a predetermined quantity of each of a plurality of reagent-mixture components, wherein each predetermined quantity corresponds to the respective input, and further controls the pump or pumps to mix the aspirated components into the reagent mixture. The control unit then controls a pump to introduce the reagent mixture through the sensing unit for sensing a particle distribution of the reagent mixture, such as for blood cell analysis.

In one embodiment of the present invention, the plurality of inputs each correspond to a respective animal species, and for each input, the plurality of reagent-mixture components includes a first reagent-mixture component consisting essentially of a whole blood sample of the respective species, a second reagent-mixture component consisting essentially of diluent, and a third reagent-mixture component consisting essentially of a lysing agent for making a blood/diluent and/or a blood/diluent/lyse reagent mixture corresponding to the respective species. Also in an embodiment of the present invention, the control unit includes a database pertaining to predetermined quantities of lysing agents necessary for formulating blood/reagent mixtures for a plurality of species. The control unit is responsive to an input indicating a specific species to control one or more pumps to aspirate, predetermined quantities of the lysing agents from the first and second lysing containers corresponding to the respective species.

One advantage of the apparatus and method of the present invention is that the reagent mixture may be automatically adjusted to correspond to each of a plurality of different operator inputs, which may each correspond, for example, to a different animal species to automatically create the reagent mixture for each species.

Other advantages of the present invention will become apparent in view of the following detailed description and accompanying drawings.

BRIEF DESCRIPTION OF THE DRAWINGS

FIG. 2 is front plan view of the pump unit of the apparatus of. FIG. 1.

DETAILED DESCRIPTION

Figure 1:
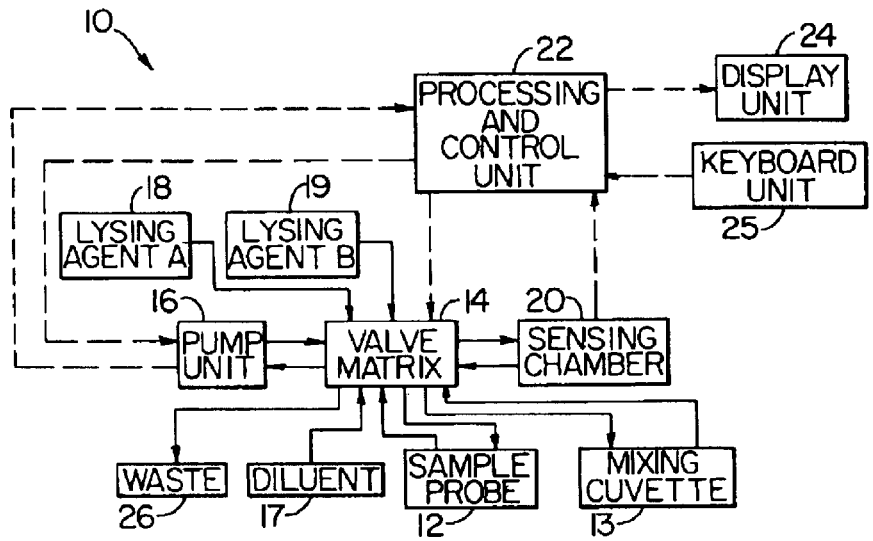
FIG. 1 is a schematic diagram of an apparatus embodying the present invention.

In FIG. 1, an apparatus embodying the present invention is indicated generally by the reference numeral 10. The apparatus 10 is employed for hematological testing, and is specifically suited for cell analysis on a wide variety of species. The apparatus 10 includes a sample probe 12 for aspirating a sample of blood to be tested. The sample probe 12 is coupled to a valve matrix 14, which in turn couples the sample probe to a selected syringe within a pump unit 16 to aspirate a predetermined volume of the blood sample into the probe (e.g., 20 μl), as is described further below.

The blood sample is discharged into a mixing cuvette 13, in which a predetermined volume of diluent and a predetermined volume of lytic reagents are rapidly admixed with the whole blood sample. The mixing cuvette 13 is coupled through the valve matrix 14 and the pump unit 16 to a first chamber or container 18 containing a first lysing agent A, and a second chamber or container 19 containing a second lysing agent B. The sample probe 12 is also coupled through the valve matrix 14 and pump unit 16 to a diluent reservoir or container 17. Thus, the sample probe 12 dispenses the blood sample along with a predetermined volume of diluent from the diluent reservoir 17 into the mixing cuvette 13. At about the same time, predetermined volumes of lysing agent A and/or lysing agent B are aspirated from the lysing chambers 18 and 19, respectively, by the pump unit 16, and injected through the valve matrix 14 into the mixing cuvette 13, along with the blood sample and diluent to formulate the sample blood/reagent mixture, as described further below. Preferably, the ratio of the individual lyse components in the lytic reagent composition are present in a ratio and quantity sufficient to effect at least a component separation of white blood cells, so that they can be differentiated, and at least one of the white blood cell subpopulations can be quantified.

The particular reagent compositions and the preferred methods for employing these compositions are disclosed in patent application Ser. No. 711,965, filed Jun. 7, 1991, now U.S. Pat. No. 5,316,725, entitled "Method And Reagent System For The Improved Determination Of White Blood Cell Subpopulations", and U.S. Pat. No. 5,262,329, entitled "Method For Improved Multiple Species Blood Analysis", which is a continuation of patent application Ser. No. 714,671, filed Jun. 13, 1991, entitled "Method And Reagent system For Improved Multiple Species Blood Analysis", now abandoned which are each hereby expressly incorporated by reference as part of the present disclosure.

The sample blood/reagent mixture remains in the mixing cuvette 13 for a short but sufficient amount of time for the red blood cells to be stromatolyzed and to release their hemoglobin, and for the active lytic reagents to act on the cell membranes of the white blood cells and cause them to selectively separate. After this short time period (e.g., approximately 10 to 30 seconds), the sample is aspirated through the valve matrix 14 into a selected syringe in the pump unit 16, as is described further below. The sample is then injected by the pump unit 16 back through the valve matrix 14 and into a sensing chamber 20 (also referred "Focused Flow™" cell) along with a diluent sheath, in which the white blood cells, are counted and the volume (size) and/or opacity is measured by electrical or optical differences. The white blood cells are counted for a period of time to gather sufficient data for analysis, typically about 10,000 cells. Data points are stored and analyzed in a processing and control unit 22, and the data can in turn be visually displayed on a display unit 24. A keyboard unit 25 is coupled to the processing and control unit 22 to control its operation. After the sample is analyzed, it is passed through the valve matrix 14 into a waste container 26 and discarded.

Figure 2:
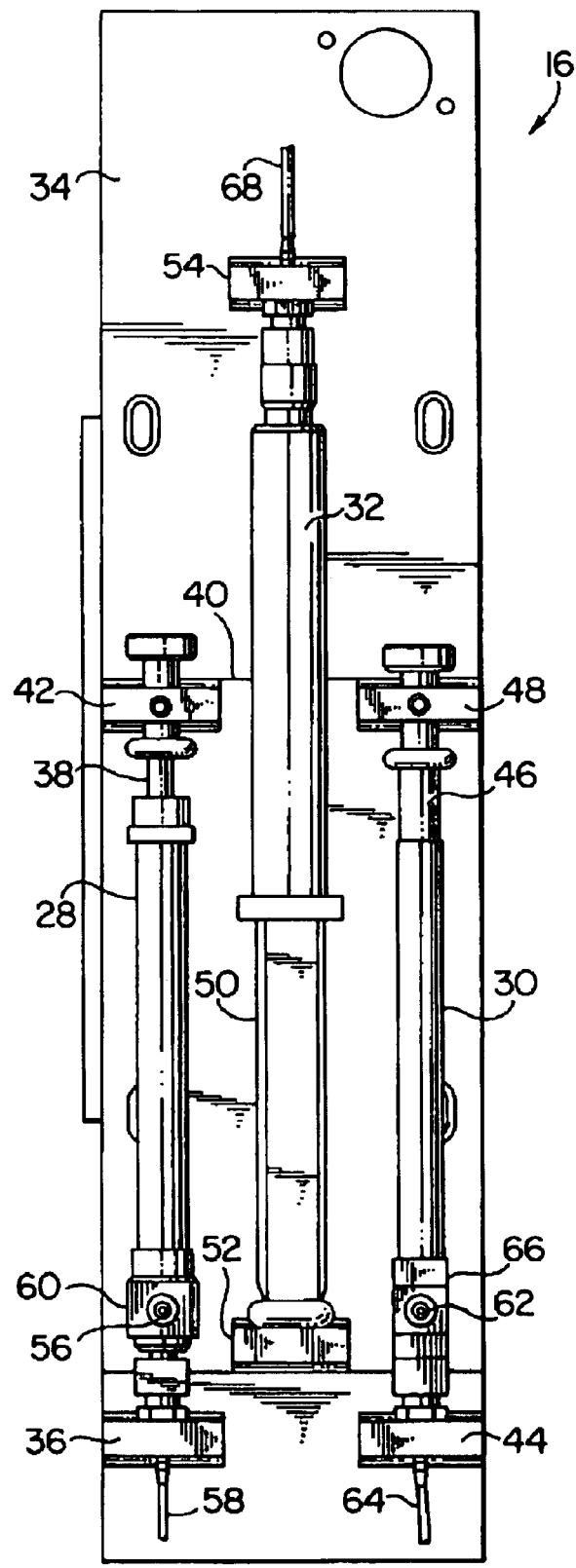
Figure 3:
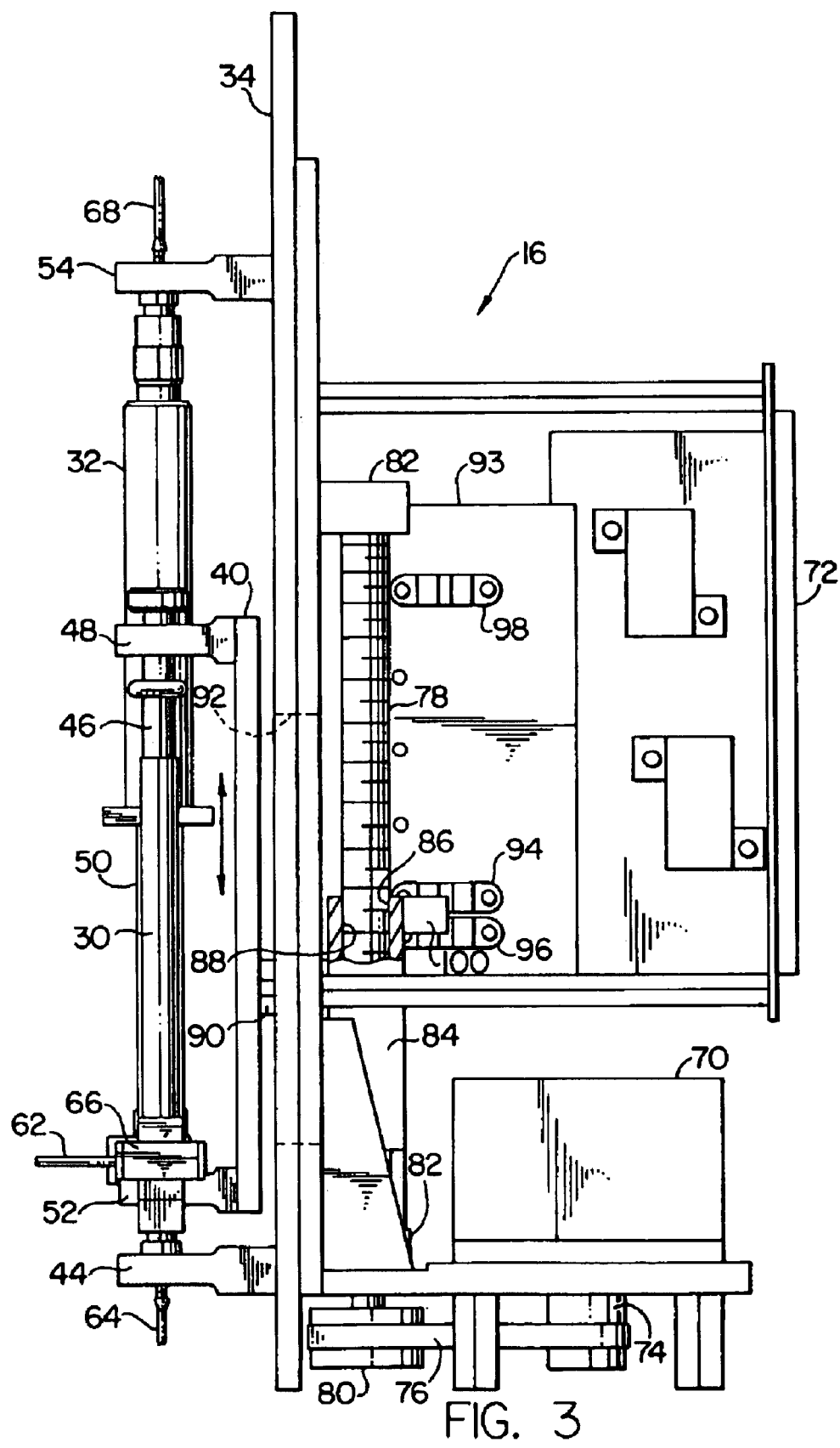
FIG. 3 is a side plan view of the pump unit of FIG. 2.

Turning to FIGS. 2 and 3, the pump unit 16 is illustrated in further detail, and includes several pumps, which in the embodiment of the present invention illustrated are positive-displacement pumps, including a first syringe 28, a second syringe 30, and a third syringe 32. Each of the syringes has a pistons (and functions as a positive-displacement pump), which can be coupled through the valve matrix 14 to any of the other fluid-containing components of the apparatus 10 in order to aspirate and/or inject the fluids, as is described further below.

One end of the first syringe 28 is mounted to a base plate 34 by a first base mount 36, and a first piston 38 of the first syringe is mounted on the other end to a drive plate 40 by a first drive mount 42. Similarly, one end of the second syringe 30 is mounted to the base plate 34 by a second base mount 44, and a second piston 46 of the second syringe is coupled on the other end to the drive plate 40 by a second drive mount 48. The third syringe 32, on the other hand, is mounted in the opposite direction of the first and second syringes, 28 and 30, respectively. A piston 50 of the third syringe 32 is coupled on one end to the drive plate 40 by a third drive mount 52, and the other end of the third syringe is coupled to the base plate 34 by a third base mount 54. By driving the drive plate 40 in the downward direction of FIG. 2, the first syringe 28 and second syringe 30 simultaneously inject fluid from the respective syringe, and the third syringe 32 simultaneously aspirates fluid into the syringe, whereas movement of the drive plate 40 in the upward direction of FIG. 2 causes the opposite to occur.

The first syringe 28 is coupled to one end of a first line 56 and coupled to one end of a second line 58 by means of a first connector 60. The other end of each of the first line 56 and second line 58 (not shown) is coupled to the valve matrix 14. The second syringe 30 likewise is coupled to one end of a first line 62 and coupled to one end of a second line 64 by means of a second connector 66. The other end of each of the first line 62 and second line 64 (not shown) is coupled to the valve matrix 14. Each of the second lines 58 and 64 are typically used for injecting and/or aspirating fluids with the respective syringe, whereas the first lines 56 and 62 are typically used for purposes of flushing diluent from the diluent reservoir 17 to clean the respective syringe and/or to wash away any air bubbles. The third syringe 32 is coupled to one end of a third line 68 for aspirating and/or injecting fluid with the third syringe. The other end of the third line 68 (not shown) is coupled to the valve matrix 14 for controlling flow through the third line.

As shown in FIG. 3, a motor 70 is coupled to the drive plate 40 to precisely move the drive plate, and in turn simultaneously control the actuation of the three syringes. In the embodiment of the present invention illustrated, the motor 70 is preferably an electric stepping motor, but may be a DC or AC electric motor with proper feedback and electronic control, and is coupled to a control board 72, which is in turn coupled to the processing and control unit 22 to control the operation of the motor. The motor 70 comprises a drive shaft 74 coupled to one side of a drive belt 76, which is in turn coupled to one end of a threaded shaft 78 by means of a gear 80. The drive belt 76 preferably defines a plurality of teeth on its inside surface which mesh with corresponding teeth on both the drive shaft 74 and the gear 80 in order to maintain precise control over the movement of these components. The drive to shaft 78 is mounted on each end by bearing blocks 82 to the base plate 34, and a drive block 84 is mounted on the threaded shaft 78. The drive block 84 includes an aperture 86 extending through the drive block and defined by a threaded surface 88, which engages the corresponding threads on the threaded shaft 78. The drive plate 40 is coupled to the drive block 84 by drive mounts 90, which extend through an elongated aperture 92 defined within the base plate 34, indicated in dashed lines in FIG. 3. As can be seen, the elongated aperture 92 extends in a direction substantially parallel to the threaded shaft 78.

By operating the stepping motor 70, the threaded shaft 78 is rotated to drive the drive block 84 along the axis of the threaded shaft 78 by engagement of the threads on the surface 88 with the threads on the shaft 78, which in turn simultaneously moves the drive plate 40 and the pistons of the three syringes. Based oh the direction of the motor 70, the first and second syringes 28 and 30, respectively, inject, and the third syringe 32 simultaneously aspirates, or viceversa.

The pump unit 16 further includes a sensor mounted adjacent the threaded shaft 78 and drive block 80 to indicate the position of the drive block and control the operation of the motor 70 in response. The sensor is mounted on a sensor control board 93, which is coupled to the drive control board 72 to transmit signals to the drive control board for controlling the operation of the motor 70. The drive control board 72 is in turn coupled to the processing and control unit 22. The sensor includes three position sensors, a home-position sensor 94, a first-end position sensor 96, and a second-end position sensor 98. The drive block 84 includes it a corresponding sensor plate or flag 100 mounted in line with the three position sensors, and adapted to cause each position sensor to generate a signal when the sensor plate is aligned with a respective position sensor.

Accordingly, when the drive block 84 is located in the home position, the home-position sensor 100 transmits a signal indicative of this condition to the control board 72. At this point, the processing and control unit 22 is responsive to this signal to recognize that both the first and second syringes are nearly empty, and the third syringe is nearly full. By counting the number of steps upon operation of the stepping motor 70 from the home position, the processing and control unit 22 can cause a precise volume of fluid to either be injected or aspirated with each syringe. The firstposition sensor 96 and second-position sensor 98 are provided as a safety back-up, each being located at one extreme of the permissible movement of the drive block 84. If either of these position sensors are activated, the drive control board 72 is responsive to stop the motor 70 to prevent any damage to the pump unit 16.

Figure 4:
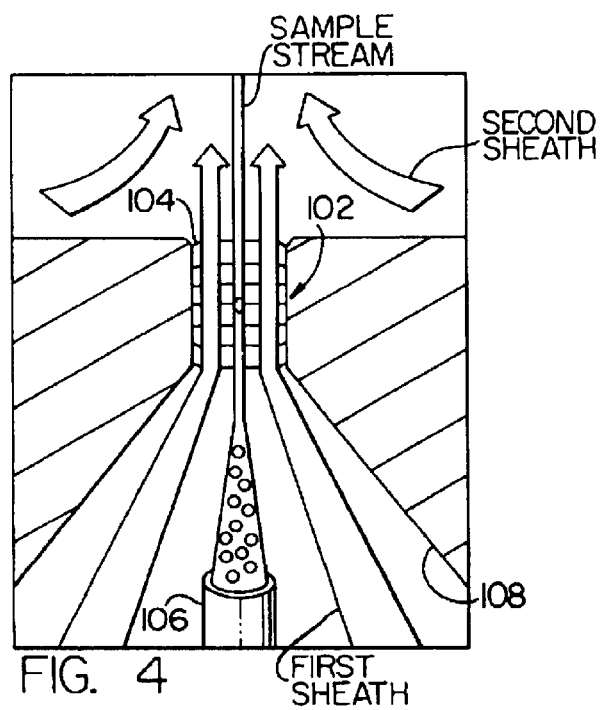
FIG. 4 is a magnified, partial schematic view of the sensing chamber of the apparatus of FIG. 1 illustrating schematically the flow of the sheath fluids and of the sample stream.
Figure 5:
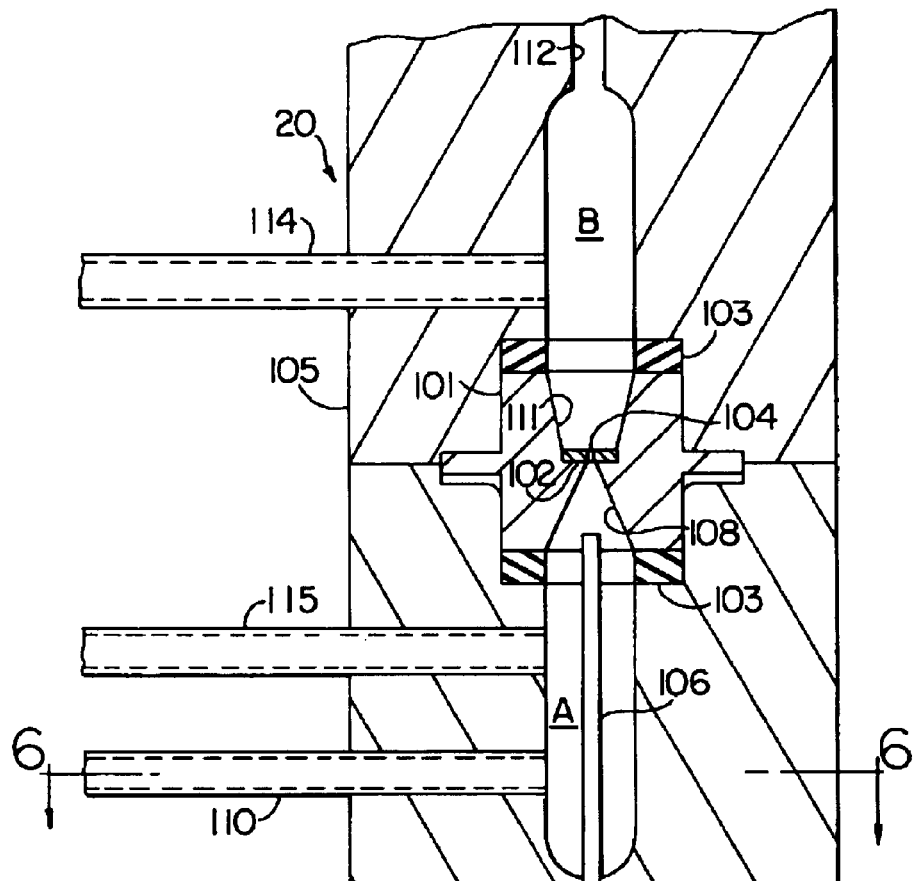
FIG. 5 is a partial detailed cross-sectional view of the sensing chamber of FIG. 1.
Figure 6:
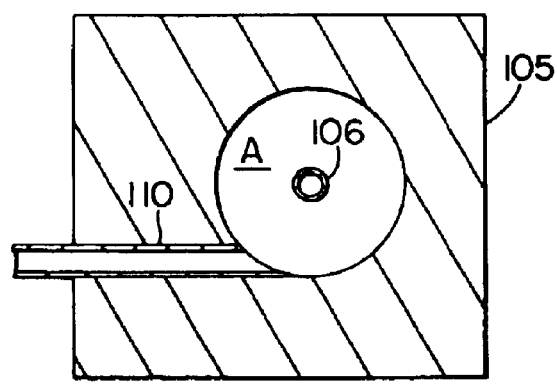
FIG. 6 is a cross-sectional view of FIG. 5 taken along the line 6—6 of FIG. 5.

Turnip to FIGS. 4–6, a portion of the sensing chamber or Focused Flow™ cell 20 is illustrated in further detail. The sensing chamber 20 includes a sensing zone 102, which defines a counting orifice 104, as shown in FIG. 4. The counting orifice 104 receives a narrow stream of the blood sample injected by one of the syringes of the pump unit 16 through the valve matrix 14 and a sample tube 106. The sample tube 106 is substantially coaxial with the counting orifice 104 and injects a narrow stream of the blood sample through the center of the orifice, as illustrated in FIG. 4. The sensing zone comprises a transducer (not shown) for detecting differences in electrical, optical, chemical or other characteristics in each of the cells of the sample, and for generating a signal whose characteristics relate to such differences. These signals are transmitted to the processing and control unit 22 where they are processed to determine the parameters of the constituent subpopulations of the sample.

The preferred components of the processing and control unit 22 for performing this function are described in patent application Ser. No. 650,686, now U.,S. Pat. No. 5,187,673 filed Feb. 5, 1992, entitled "Method And Apparatus For Determining The Distribution Of Constituent Subpopulations Within A Population Of Particles Having Overlapping Subpopulations", which is hereby expressly incorporated by reference as part of the present disclosure.

As shown in FIGS. 4 and 5, the sensing chamber 20 includes a sensing unit 101, which defines a substantially conical-shaped surface 108 for receiving a sheath of diluent surrounding the sample stream injected by the sample tube 106. The sensing unit 101 is mounted by means of a pair of o-rings 103 within a support block 105. The support block 105 defines a generally cylindrical chamber A coupled in fluid communication, and substantially concentric with the conical-shaped surface 108. As shown in FIG. 5, the sample tube 106 is mounted within the center of the chamber A and extends into the recess defined by the conical-shaped surface 108. A first sheath or diluent tube 110 is coupled on one end to the chamber A, and in the embodiment of the present invention illustrated, is oriented substantially along a tangent to the cylindrical surface defining the chamber A, as shown in FIG. 6. The other end of the first sheath tube 110 is coupled through the valve matrix 14 to another of the syringes in the pump unit 16, for receiving a predetermined volume of diluent injected by that syringe. Because the first sheath tube 110 is oriented on a tangent to the cylindrical surface of the chamber A, the diluent follows a generally spiral or helical path through the chamber A, along the conical-shaped surface 108, and through the counting orifice 104 surrounding the sample stream, as indicated by the arrows in FIG. 4. This particular orientation of the first sheath tube 110 is only exemplary, however. For example, one or more first sheath tubes may equally be oriented so that the diluent flows straight along the conical-shaped surface 108 and through the counting orifice 104.

The sensing unit 101 defines a tapered surface 111 on the exit side of the counting orifice 104, which is coupled in fluid communication with a chamber B for receiving the sample stream and diluent injected through the counting orifice. An exit tube 112 is coupled on one end to the chamber B, and is coupled on the other end (not shown) through the valve matrix 14 to a selected syringe of the pump unit 16 to aspirate the sample/diluent mixture injected through the counting orifice 104 into the chamber B and exit tube 112, into the respective syringe.

A second sheath tube 114 is coupled on one end in fluid communication with the chamber B between the o-ring 103 and the exit tube 112. As with the first sheath tube 110, in the embodiment of the present invention illustrated, the second sheath tube 114 is oriented substantially on a tangent to the cylindrical surface defining the chamber B so that the diluent is aspirated into the chamber B and exit tube 112 along a substantially spiral or helical path surrounding the sample stream injected through the counting orifice 104. As with the first sheath tube 110, this particular configuration of the second sheath tube 114 is only exemplary, however. The other end of the sheath tube 114 is coupled through the valve matrix 14 to the diluent reservoir 17.

As shown in FIG. 5, a third diluent tube 115 is coupled to the chamber A between the o-ring 103 and the first diluent tube 110, and is likewise oriented along a tangent to the cylindrical surface defining the chamber A. The other end of the third diluent tube 115 is coupled through the valve matrix 14 to the diluent reservoir (or syringe) for flushing the sensing chamber 20 with fresh diluent after running a sample.

In the operation of the apparatus of the present invention, a whole blood sample is introduced into the sample probe 12. The processing and control unit 22 connects the sample probe 12 to a selected syringe of the pump unit 16 through the valve matrix 14, and then controls the motor 70 to aspirate a predetermined volume of the whole blood sample (e.g., 20 µl) through the probe. The processing and control unit 22 also connects the same syringe through the valve matrix 14 to the diluent reservoir 17, and controls the motor 70 to aspirate a predetermined volume of diluent into the whole blood sample. The processing and control unit 22 then controls the motor 70 to inject the sample/diluent mixture from the syringe through the valve matrix 14 into the mixing cuvette 13.

The processing and control unit 22 has in a database information as to the predetermined volumes of lysing agent A and lysing agent B necessary to form the proper sample blood/reagent mixture for selected animal species (e.g., dog, cat, rat, mouse, horse, cow, rabbit, monkey, pig, goat, bird, etc.). The operator inputs through the keyboard unit 25 the particular animal species of the blood sample, and the processing and control, unit 22 is responsive to this input based on the information in its database to select a predetermined volume of lysing agent A and a predetermined volume of lysing agent B. The processing and control unit 22 then connects a selected syringe in the pump unit 16 to the lysing agent A chamber 18 through the valve matrix 14, and controls the motor 70 (by counting a predetermined number of steps) to aspirate the predetermined volume of lysing agent A by the syringe. The processing and control unit 22 then connects the same syringe (or another syringe) to the lysing agent B chamber 19 through the valve matrix 14, and controls the motor 70 (by counting a predetermined number of steps) to aspirate the predetermined volume of lysing agent B by the syringe. The processing and control unit 22 then couples the syringe through the valve matrix 14 to the mixing cuvette 13, and controls the motor 70 to inject the predetermined mixture of lysing agent A and lysing agent B into the mixing cuvette with the blood/diluent mixture.

After the sample blood/reagent mixture is prepared in the mixing cuvette 13, the processing and control unit 22 couples the second line 58 of the first syringe 28 in fluid communication with the mixing cuvette 13 by actuating a valve (not shown) in the valve matrix 14 to aspirate a predetermined volume of sample blood/reagent mixture into the first syringe. In the embodiment of the present invention illustrated, the volume of the first syringe 28 is 250 µl. The processing and control unit 22 also couples the second inlet line 62 of the second syringe 30 in fluid communication with the diluent reservoir 17 by actuating a valve (not shown) in the valve matrix 14, to aspirate a predetermined volume of diluent into the second syringe. In the embodiment of the present invention illustrated, the volume of the second syringe 30 is approximately 250 µl. The precise volume of fluid aspirated into each syringe is controlled by the processing and control unit 22, which counts the number of steps of the motor 70 with respect to the home position as indicated by the home-position sensor 94, wherein each step corresponds to a precise volume of fluid for each if syringe.

The valves permitting this aspiration of the first and second syringes 28 and 30, respectively, are then closed, and the processing and control unit 22 actuates additional valves in the valve matrix 14 to couple the secondline 58 of the first syringe 28 in fluid communication with the sample tube 106 of the sensing chamber 20, and to couple the second line 64 of the second syringe 30 in fluid communication with the first diluent tube 110 of the sensing chamber 20. The processing and control unit 22 also then actuates selected valves of the valve matrix 14 to couple the third line 68 of the third syringe 32 in fluid communication with the exit tube 112 of the sensing chamber 20, and to couple the second diluent tube 114 in fluid communication with the diluent reservoir 17. The system is then ready to analyze the sample.

The processing and control unit 22 then actuates the motor 70 to drive the drive block 84 back toward the home position. This in turn causes the first and second syringes 28 and 30, respectively, to simultaneously inject the sample blood/reagent mixture through the sample tube 106 and the diluent through the first diluent tube 110. As illustrated in FIG. 4, a narrow stream of blood/reagent mixture is thus injected by the first syringe 28 through the center of the counting orifice 104, and a stream of diluent is injected by the second syringe 30 into the chamber A, along the substantially conical-shaped surface 108, and through the counting orifice 104 along a path which surrounds the stream of sample blood/reagent mixture, but substantially avoids if any intermixing of the two streams. In the embodiment of the present invention illustrated, the counting orifice is approximately 60 microns in diameter, the sample stream is approximately 15 microns in diameter, and the sheath of diluent is therefore approximately 35 microns thick within the counting orifice, surrounding the sample stream.

Because both the flow of the diluent sheath injected through the first diluent tube 110 is substantially laminar, and the sample stream injected through the sample tube 106 is substantially laminar, there is substantially no intermixing of the two streams. The steady state flow generated by the syringes significantly facilitates in producing a substantially laminar flow. Also, because the sample stream is located in the approximate center of both the recess defined by the conical-shaped surface 108 and the counting orifice 104, it moves at a relatively faster velocity through the counting orifice than does the surrounding sheath of diluent, thus further preventing any intermixing of the sample and diluent. Also, the sheath of diluent, which in the embodiment of the present invention illustrated follows a generally spiral or helical path as it is injected through the first diluent tube 110, the chamber A, and along the conical-shaped surface 108, surrounds the sample stream with a substantially laminar flow, and thus tends to maintain the sample flow in a fine, substantially uniform stream located in the center of the counting orifice. The flow of the diluent sheath also tends to maintain the sample stream within the center of the counting orifice.

As the first and second syringes 28 and 30, respectively, simultaneously inject the sample and the diluent into the front end of the sensing chamber 20, the third syringe 32 simultaneously aspirates the sample/diluent mixture injected into the outlet side of the counting orifice 104, and also aspirates a second sheath of diluent through the second diluent tube 114 into the exit tube 112. Because the second diluent tube 114 is oriented along a tangent to the surface defining the chamber B, the second sheath of diluent follows a substantially spiral flow path surrounding the sample stream exiting the counting orifice 104. The substantially laminar flow of the second sheath acts to further maintain the sample in a fine, narrow stream as it exits the counting orifice, thus further increasing the ability of the sensing chamber to accurately analyze the sample cells.

The processing and control unit 22 stops the motor 70 after a predetermined volume of the blood sample has been injected by the first syringe 28. In the embodiment of the present invention illustrated, the volume of the third syringe 32 is approximately 5 ml, which is sufficient to receive the entire volume of fluid injected by both the first and second syringes 28 and 30, respectively, and to aspirate a sufficient volume of diluent through the second diluent tube 114 to form the second diluent sheath in the exit tube 112.

The processing and control unit 22 then actuates a selected valve in the valve matrix 14 to couple the third line 68 of the third syringe 32 in fluid communication with the waste reservoir 26, and the motor 70 is then actuated in the opposite direction (i.e., away from the home position) to expel the sample/diluent mixture in the third syringe into the waste reservoir 26.

One advantage of the illustrated embodiment of the present invention, is that because the three syringes are simultaneously driven by the stepping motor, there is a simultaneous, steady-state flow of both the sample and diluent through the counting orifice. The smooth and precise operation of the stepping motor in combination with the direct drive of the threaded shaft and drive plate and the positive-displacement pumping of the syringes, permits precise, simultaneous control of the fluid flow through the sensing chamber. As a result, the flow of both diluent sheaths and the sample stream is substantially laminar, thus substantially preventing any mixing of these fluids within the counting orifice. Also, as described above, the first sheath of diluent can be injected, or aspirated, along a substantially spiral path through the counting orifice and surrounding the sample stream (which can be aspirated or injected), which also facilitates in maintaining a fine, narrow sample stream through the counting orifice. Moreover, the second sheath of diluent, which is likewise substantially laminar, and can be injected or aspirated along a substantially spiral path surrounding the sample stream, further contributes to maintaining a fine, narrow sample stream as the sample exits the counting orifice.

Thus, there is a steady, repeatable flow of sample and diluent through the counting orifice each time a sample is injected. Moreover, because the sample stream is maintained in a fine, narrow configuration, the platelets, red blood cells or white blood cells of the sample are oriented in a substantially single file relationship relative to each other as they pass through the counting orifice, thus permitting the sensing chamber to detect approximately one cell at a time, and accumulate data in this fashion on thousands of cells. Accordingly, coincidence, or the passage of multiple cells at once through the counting orifice is substantially avoided. Moreover, the cells flow through the counting orifice in a substantially steady state, which is repeated from one sample to the next. The anomalies or aberrant information normally associated with coincidence, are substantially avoided. In addition, because substantially each cell in the sample is detected (due to the substantially single file relationship of the cells), important information is not rejected, enabling the system to provide a more true measurement of the cell distribution within each sample.

Another advantage of the embodiment of the present invention illustrated, is that because only one drive has to be used to simultaneously drive all three syringes, which then assures that all three syringes move simultaneously. Also, there is a significant cost savings as opposed to a system in which a separate drive may be employed for each syringe.

Yet another advantage of the embodiment of the present invention illustrated, is that because the sample and sheath are injected through the inlet side of the counting orifice (as opposed to either being pulled or aspirated only through the orifice), deformation of the cells as they flow through the orifice is substantially avoided. Cell distortion is therefore reduced to a minimum, further enhancing the accuracy of the system and providing hematocrit measurements that accurately correlate with spun hematocrits.

Yet another advantage of the illustrated embodiment of the present invention, is that the three pumps or syringes can be employed to inject and/or aspirate different fluids simply by adjusting the connections with the syringes in the valve matrix. For example, it may be desirable to employ the second syringe 30 to inject diluent through the second diluent tube 114. In this case, the first diluent sheath is aspirated through the counting orifice by the third syringe 32, whereas the sample stream and the second sheath are injected by the first and second syringes, respectively. It may equally be desirable to mount the third syringe 30 in the same direction and in the same fashion to the drive plate 40 and base plate 34 as are the first and second syringes 28 and 30, respectively. In this case, the first syringe 28 may inject the sample, the second syringe 30 may inject the first diluent sheath, and the third syringe 32 may inject the second diluent sheath. In this situation, the exit tube 112 would be coupled in fluid communication with the waste reservoir 26 in order to release the sample/diluent mixture directly into the waste reservoir.

Another advantage of the illustrated embodiment of the present invention is that the steady state, unique flow produced by the syringes minimizes protein build-up and clogging. First, the first and second diluent sheaths maintained around the sample cells prevents contact of the sample cells with the walls of both the sensing chamber and the exit tube. Second, because the sample blood/reagent mixture is powerfully injected through the counting orifice by one of the syringes, clogs and build-up within each cycle are prevented.

Another advantage of the present invention, is that the processing and control unit can automatically optimize sample analysis on a species-by-species basis. The database of the processing and control unit can contain information on the predetermined volumes of the lysing agents for all species encountered in this type of hematology system. Thus, the operator does not need to be concerned with preparing the specific blood/reagent mixture for each type of species being tested. Rather, the operator simply inputs the type of species on the keyboard unit, and the processing and control unit automatically determines the quantities of the lysing agents based on the type of species, and then automatically controls the operation of the pump unit to aspirate the predetermined volumes of lysing agents, and to mix them with the sample/diluent mixture in the mixing cuvette.

In one embodiment of the present invention, the keyboard unit has separate keys for certain species (e.g., cat and dog) and another key for other species. Thus, by pressing the "cat" key or the "dog" key, the processing and control unit automatically causes the preparation of the blood/reagent mixture for the respective species. By pressing the "other" key, the display unit displays the additional species may be processed. Once the correct species is selected, the processing and control unit automatically causes the preparation of the blood/reagent mixture for the respective species.

Another advantage of the present invention is the flexibility of the system to adapt to automatically analyze samples from numerous types of species, and to optimize any cycle for a given species. For example, the lyse volumes, the volume of diluent, and the volume of the whole blood sample, can be easily adjusted simply by controlling the processing and control unit. This can be extremely beneficial for analyzing species that are very different, such as mammalian vs. non-mammalian. Moreover, because the pump unit employs several different, pumps to aspirate, or inject or otherwise pump these fluids, the apparatus can automatically mix two or more of these fluids in predetermined volumes, which are precisely measured by monitoring operation of the stepping motor, which is a significant advantage over prior hematology systems. As illustrated above, the volume of lyse A and/or the volume of lyse B (and other lyse agents may be added if necessary) can be automatically adjusted and mixed with the blood/diluent mixture in the mixing cuvette to effect proper separation of blood cells on a species-by-species basis. This means for variably adjusting the volume of lytic agents is significant in obtaining the proper separation of the white blood cell populations.

What is claimed is:

1. A method for making a plurality of different reagent mixtures comprising blood and analyzing particle distributions of the reagent mixtures, wherein each reagent mixture corresponds to a respective operator input indicative of a respective species of blood, and the method is performed with an apparatus having at least one pump, at least one reagent chamber containing at least one lysing agent, a sensing unit defining a counting orifice for receiving a reagent mixture and analyzing a particle distribution of the reagent mixture, and a control unit responsive to each operator input to control the at least one pump to make a respective reagent mixture having a volumetric ratio of the at least one lysing agent to blood corresponding to the respective operator input and species of blood, and to further control the sensing unit to analyze a particle distribution of the reagent mixture, the method comprising the following steps:

adjusting the volumetric ratio of the at least one lysing agent to blood, in response to an operator input indicative of a respective species of blood, to correspond to the respective operator input, and thereby form a predetermined reagent mixture corresponding to the respective operator input and species of blood, said adjusting including:

selecting at least one lysing agent corresponding to the respective operator input;

pumping with the at least one pump a predetermined volume of the at least one lysing agent corresponding to the respective operator input;

pumping with the at least one pump a predetermined volume of blood corresponding to the respective operator input;

intermixing the predetermined volumes of the at least one lysing agent and blood, and in turn creating the predetermined reagent mixture corresponding to the respective operator input; and introducing the predetermined reagent mixture through the counting orifice of the sensing unit and sensing a particle distribution of said reagent mixture.

2. A method as defined in claim 1, further comprising the steps of:

in response to each of a plurality of different operator inputs, selecting the ratio of blood to the at least one lysing agent in the corresponding reagent mixture;

pumping with the at least one pump a predetermined volume of the at least one selected lysing agent corresponding to the respective blood/lysing agent ratio;

pumping with the at least one pump a predetermined volume of blood corresponding to the respective blood/lysing agent ratio; and intermixing the predetermined volumes of blood and the least one lysing agent, and in turn creating a reagent mixture corresponding to the respective operator input.

3. A method as defined in claim 2, further comprising the steps of:

in response to each of a plurality of operator inputs, selecting the ratio of blood to at least one first lysing agent and at least one second lysing agent in the respective reagent mixture;

pumping with the at least one pump a predetermined volume of the at least one first lysing agent corresponding to the respective blood/lysing agent ratio;

pumping with the at least one pump a predetermined volume of the at least one second lysing agent corresponding to the respective blood/lysing agent ratio;

pumping with the at least one pump a predetermined volume of blood corresponding to the respective blood/lysing agent ratio; and intermixing the predetermined volumes of blood and the first and second lysing agents, and in turn creating a reagent mixture corresponding to the respective operator input.

4. A method as defined in claim 1, further comprising-the steps of:

providing a database comprising data indicative of (i) a plurality of animal species, and (ii) a plurality of different reagent mixtures and the predetermined volumes of the reagent mixture components of each reagent mixture, wherein each reagent mixture corresponds to one or more of the plurality of animal species;

in response to each operator input corresponding to a respective one of the plurality of animal species, selecting one of the plurality of reagent mixtures corresponding to the respective animal species; and pumping with the at least one pump the predetermined volumes of the reagent-mixture components, and in turn creating the reagent mixture corresponding to the respective animal species.

5. A method as defined in claim 4, wherein the reagent-mixture components include (i) a predetermined volume of blood, and (ii) a predetermined volume of diluent.

6. An apparatus for making a plurality of reagent mixtures comprising blood and analyzing particle distributions of the reagent mixtures, comprising:

at least one pump;

at least one reagent chamber coupled in fluid communication with the at least one pump and containing at least one lysing agent;

a sensing unit defining a counting orifice for receiving a reagent mixture and analyzing a particle distribution of the reagent mixture; and means for adjusting the volumetric ratio of blood to the at least one lysing agent for creating a plurality of different reagent mixtures, each corresponding to a respective operator input indicative of at least one respective species of blood, and for controlling the at least one pump in response to each operator input to pump predetermined volumes of blood and the at least one lysing agent in accordance with the blood/lysing agent ratio corresponding to the respective operator input and species of blood, said means further controlling the at least one pump to (i) intermix the predetermined volumes of blood and the at least one lysing agent and thereby create the reagent mixture corresponding to the respective operator input, and (ii) introduce the reagent mixture through the counting orifice of the sensing unit for sensing a particle distribution of the reagent mixture.

7. An apparatus as defined in claim 6, wherein the means for adjusting the volumetric ratio is defined by a control unit.

8. An apparatus for making a plurality of reagent mixtures for multi-species hematology testing, and for sensing particle distributions of the mixtures for multi-species hematology analysis, comprising:

at least one reagent chamber for containing at least one lysing agent;

at least one pump coupled in fluid communication with the at least one reagent chamber;

a mixing chamber coupled in fluid communication with the at least one pump for receiving the at least one lysing agent and a predetermined volume of a blood specimen corresponding to any one of a plurality of different species;

a control unit electrically coupled to the at least one pump for adjusting the volumetric ratio of the blood specimen to the at least one lysing agent in correspondence with an operator input corresponding to a respective one of the plurality of species and, in turn, creating a reagent mixture therefrom having a blood to lysing agent volumetric ratio corresponding to the operator input and respective species; and a sensing unit coupled in fluid communication with the at least one pump and defining at least one counting orifice for receiving a reagent mixture and analyzing a particle distribution of the reagent mixture.

9. An apparatus for making a plurality of reagent mixtures for multi-species hematology testing, and for sensing particle distributions of the mixtures for multi-species hematology analysis, comprising:

first means for containing at least one lysing agent;

second means coupled in fluid communication with the first means for pumping the at least one lysing agent;

third means coupled in fluid communication with the second means for receiving the at least one lysing agent and a predetermined volume of a blood specimen corresponding to any one of a plurality of different species;

fourth means electrically coupled to the second means for adjusting the volumetric ratio of the blood specimen to the at least one lysing agent in correspondence with an operator input corresponding to a respective one of the plurality of species and, in turn, creating a reagent mixture therefrom having a blood to lysing agent volumetric ratio corresponding to the operator input and respective species; and fifth means coupled in fluid communication with the second means for receiving a reagent mixture and analyzing a particle distribution of the reagent mixture.

10. An apparatus as defined in claim 9, wherein the first means is defined by at least one reagent chamber for containing the at least one lysing agent.

11. An apparatus as defined in claims 9, wherein the second means is defined by at least one pump coupled in fluid communication with the first means for pumping the at least one lysing agent.

12. An apparatus as defined in claim 9, wherein the third means is defined by a mixing chamber coupled in fluid communication with the second means.

13. An apparatus as defined in claim 9, wherein the fourth means is defined by a control unit.

14. An apparatus as defined in claim 9, wherein the fit means is defined by a sensing unit defining a counting orifice for receiving a reagent mixture and analyzing a particle distribution of the reagent mixture.

* * * * *

UNITED STATES PATENT AND TRADEMARK OFFICE
CERTIFICATE OF CORRECTION

PATENT NO. : 6,812,032 B1
DATED : November 2, 2004
INVENTOR(S) : Carver, Jr. et al.

It is certified that error appears in the above-identified patent and that said Letters Patent is hereby corrected as shown below:

<u>Title page,</u>
Item [75], Inventors, please delete "David Charles, DeCava, Oxford, CT (US)".

Signed and Sealed this

Fifteenth Day of November, 2005

JON W. DUDAS
*Director of the United States Patent and Trademark Office*